United States Patent [19]

Annis et al.

[11] Patent Number: 4,825,454
[45] Date of Patent: Apr. 25, 1989

[54] TOMOGRAPHIC IMAGING WITH CONCENTRIC CONICAL COLLIMATOR

[75] Inventors: Martin Annis, Cambridge; Michael Johnson, Southborough; Richard Mastronardi, Medfield, all of Mass.

[73] Assignee: American Science and Engineering, Inc., Cambridge, Mass.

[21] Appl. No.: 137,982

[22] Filed: Dec. 28, 1987

[51] Int. Cl.$^4$ .......................................... G01N 23/201
[52] U.S. Cl. ...................................... 378/87; 378/147; 378/86; 250/363.01
[58] Field of Search .................... 378/4, 7, 10, 11, 19, 378/86, 87, 145–147, 149, 15.4, 21, 22, 26; 250/363 SH

[56] References Cited

U.S. PATENT DOCUMENTS

| | | | |
|---|---|---|---|
| 1,352,198 | 9/1920 | MacLagan | 378/147 |
| 1,865,441 | 7/1932 | Mutscheller | 378/145 |
| 3,106,640 | 10/1963 | Oldendorf | 250/52 |
| 3,143,651 | 8/1964 | Giacconi et al. | 250/105 |
| 3,197,638 | 7/1965 | Sinclair | 250/83.3 |
| 3,373,286 | 3/1968 | Han | 378/147 |
| 3,919,557 | 11/1975 | Berninger | 250/366 |
| 3,935,462 | 1/1976 | de Luca et al. | 250/369 |
| 3,973,127 | 8/1976 | Matsuda et al. | 250/445 T |
| 3,976,885 | 8/1976 | Brunnett et al. | 250/445 T |
| 3,979,594 | 9/1976 | Anger | 250/369 |
| 4,029,964 | 6/1977 | Ashe | 250/368 |
| 4,034,218 | 7/1977 | Turcotte | 250/269 |
| 4,124,804 | 11/1978 | Mirell | 378/87 |
| 4,147,618 | 4/1979 | Richardson et al. | 209/589 |
| 4,213,054 | 7/1980 | Doherty, III | 250/505 |
| 4,229,651 | 10/1980 | Danos | 250/272 |
| 4,258,256 | 3/1981 | Harding | 250/272 |
| 4,258,428 | 3/1981 | Woronowicz | 364/527 |
| 4,302,675 | 11/1981 | Wake et al. | 250/363 S |
| 4,423,522 | 12/1983 | Harding | 378/87 |
| 4,434,369 | 2/1984 | Metal | 250/363 S |
| 4,476,385 | 10/1984 | Wunderlich | 250/303 |
| 4,495,636 | 1/1985 | Jacobs et al. | 378/87 |

FOREIGN PATENT DOCUMENTS 2939146   4/1981   Fed. Rep. of Germany ........ 378/86

OTHER PUBLICATIONS

Kuhl et al., "Image Separation Radioisotope Scanning", *Radiology*, vol. 80, Jan–Jun. 1963, pp. 653–661.
Lale, "The Examination of Internal Tissues, using Gamma-Ray Scatter with a Possible Extension to Megavoltage Radiography", *Phys. Med. Biol.* 1959, 159–167.
Tilley et al., "Dynamic Radiography-a Technique Employing Scattered Radiation to Monitor Surface Motion", *Medical and Biological Engineering*, Mar. 1976, pp. 146–150.
Towe et al., "X-Ray Compton Scatter Imaging Using a High Speed Flying Spot X-Ray Tube", *IEEE Transactions on Biomedical Engineering*, vol. BME-28, No. 10, Oct. 1981, pp. 717–721.

*Primary Examiner*—Craig E. Church
*Assistant Examiner*—John C. Freeman
*Attorney, Agent, or Firm*—Pollock, Vande Sande & Priddy

[57] ABSTRACT

An X-ray imaging apparatus comprising an X-ray source, a collimator, and an X-ray scatter detector. The X-rays are directed toward an object to be imaged where the collimator and detector are located between the source and object. The X-rays striking the object produce back scattered X-rays which are directed back through the collimator to the detector and an image is produced.

15 Claims, 2 Drawing Sheets

IMPLEMENTATION WITH VERTICAL MOTION

TOMOGRAPHIC IMAGING WITH CONCENTRIC CONICAL COLLIMATOR

TECHNICAL FIELD

The invention relates to imaging using penetrating radiant energy and more particularly to apparatus useful in producing tomographic images.

BACKGROUND ART

Imaging using penetrating radiation has been applied for the generation of images using a variety of techniques. The oldest technique produces an image (typically on X-ray film, although not necessarily) which is referred to as a shadowgraph. Because of the disadvantages of shadowgraphs, i.e. it gives a line of sight projection of the object whose image has been produced, improvements have long been sought. Tomography, i.e. the production of an image representing a slice or plane through an object being examined, has been a long-felt need. Techniques are available for the production of tomographic images or tomograms, although the presently known techniques all have various drawbacks.

One of those techniques is illustrated by Olendorf in U.S. Pat. No. 3,106,640. He mentions complicated mechanical techniques such as planigraphy, tomography, laminography and the like, which typically involve the synchronous motion, at identical angular rates, of a radiation source and a recording plane which is sensitive to the radiation. In principle, motion during the exposure period theoretically blurs everything not on a plane parallel to the plate and on the axis of rotation. This provides a sectional radiograph (or tomograph) of a layer of the object under consideration, which layer has a vague and indefinite thickness. Thus, the mechanical isolation of the layer or section from other detail is quite poor. Other techniques similar to Olendorf are shown by Ander U.S. Pat. No. 3,979,594; Brunnett U.S. Pat. No. 3,976,885; Matsuda U.S. Pat. No. 3,973,127 and deLuca U.S. Pat. No. 3,935,462.

Since the 1970's, a far more popular tomographic technique and one which has achieved widespread success is referred to as computed tomography, relying in the main on the work of Hounsfield and Cormack, for which they jointly received a Nobel prize. While there are a variety of specific techniques comprehended under the term "computed tomography", for our purposes they can all be described together. In computed tomography, an object is illuminated by a beam of penetrating radiation (in some cases this is a fan beam illuminating the object from edge to edge, in other cases it might be one or a plurality of pencil beams). A detector or detectors records the X-ray energy emitted by the object as a result of the illumination. In some fashion or another, the angular relation between the object and the source/detector arrangement is altered and the process is repeated. This is repeated a relatively large number of times, so that the X-ray energy transmitted through the plane of interest is recorded through a plurality of paths and at a plurality of angles. This data is then used as the input to a computer which generates a cross-sectional image of the section of the object that had been illuminated.

Notwithstanding the popularity of computed tomography, there are a number of major disadvantages with this technique. Firstly, in order to obtain the desired image, the object must be illuminated from edge to edge and the X-ray response of the object throughout this region must be recorded. In other words, even if we are aware that our interest is centered on a particularly known region of a known slice of the object, the entire slice must be illuminated and the data taken from that entire slice must be used before we can produce the image that we desire. Secondly, the image is not produced in real time and in fact there is a delay while the computer portion of the equipment operates on the data that has been recorded before the image is available. The necessity for the rotation poses a number of disadvantages. In a very practical sense it limits the slice orientations that are available. Consider for example the human body. Obtaining a slice which is essentially horizontal with respect to a vertically standing individual requires that relative rotation be effected about an axis which is vertical; that is the typical configuration of most popular machines. However, if one happens to desire a vertical slice relative to a vertical individual, then the human body must be rotated about a horizontal axis, i.e. the human body must be rotated head to foot. We do not know of any practical machines which are capable of this type of rotation. A significant limitation of computed tomography is the fact that the contrast at any region of the image is ultimately limited by the statistical fluctuation or noise in that region. It is a characteristic of CT that if there is a large attenuation of an X-ray beam traversing any part of the image, the entire image becomes more noisy.

A device for producing tomographic images which does not exhibit the prior art disadvantages is described in copending application Ser. No. 888,019, filed July 22, 1986 and assigned to the assignee of this application. The device described in application Ser. No. 888,019 uses a flying spot beam illuminating radiation and a line collimator; the subject matter of the above-referenced application is incorporated herein by this reference. The image produced by the device described in the copending application comprising the image of a slice is made up of a sequence of line images, each representing the radiant energy response of that portion of the object being imaged lying along a line within the slice. By providing relative motion between the object being imaged and the source/detector assembly, an image of the entire slice is produced. It is a distinct advantage of the apparatus described in the copending application that the only motion required for the production of the tomographic image is that motion to bring different "lines" of the object into the field of view of the collimator. On the other hand, the apparatus described in the copending application has a disadvantage in that images produced are subject to degradation caused by multiple scattering events in the object being imaged as a consequence of its illumination by the penetrating radiant energy.

Accordingly, it is an object of the invention to provide a device capable of producing tomographic images which does not require the computing power required by computed tomography and which has the signal to noise ratio advantages over the computed tomography similar to those exhibited by the apparatus of the copending application but which is more resistant to image degradation caused by multiple scattering.

It is another object of the present invention to provide for tomographic imaging using penetrating radiant energy which does not require the complex motion typical of computed tomography and which does not require the object being imaged to be illuminated edge to edge as is required in computed tomography.

These and other objects of the invention will become more apparent in the course of the following description.

SUMMARY OF THE INVENTION

In accordance with the invention, a source of penetrating radiant energy is employed, the radiation emitted by the source is formed into a beam of defined cross-section (preferably a so-called pencil beam) and directed along a path to a target volume. Apparatus is provided to support an object to be imaged in the target volume so that the beam intercepts the object. The invention provides a focused collimator and a scattered radiation detector assembly. The focused collimator is located between the target volume and the source and comprises a plurality of concentric frustoconical wall sections with adjacent pairs of the wall sections defining scattered radiation transmitting pathways. All of the pathways defined by the collimator originate in a region of the object through which the illuminating beam passes. The collimator includes an axial passageway coincident with the rotational axis of all of the frustoconical wall sections and colinear with the path of the radiation beam.

A scattered radiation detector assembly is located adjacent the focused collimator and closer to the source of radiant energy than the collimator. The scattered radiation detector assembly responds to scattered radiation travelling the pathways defined by the focused collimator. The scattered radiation detector assembly has an annular cross-section with a central opening colinear with the path of the radiation beam.

The conical collimator employed in the invention provides a selection, out of all the scattered radiation, of scattered radiation selected from the focal point of the collimator. In this fashion the radiation response of the focal point is detected by the scattered radiation detector assembly.

Relative motion is provided between the object being imaged on the one hand and the radiation source and focused collimator on the other hand; this relative motion is provided in two different directions. Relative motion is provided in a first direction so that the beam of penetrating radiation traverses a line in space; the collimator assembly is moved along with the radiation beam so that the focal point moves along with the radiation beam to scan a line in space. Once the scanning of a particular line in space has been accomplished (and this scanning may be repeated several times) motion is provided perpendicular to the line in space, so that as a function of time the line in space being scanned occupies a plurality of different successive positions in the object. The concatenation of the lines in space being scanned form the slice whose image is produced by the apparatus. From the preceding description, it will be apparent that while the slice being imaged may be planar, that is not essential. With appropriate motion vectors, a slice may consist of any distribution of "lines".

An important characteristic of the particular conical collimator employed in the invention is its efficiency. The ideal collimator would filter or block out scattered photons which did not originate at the focal point but pass on to the detector assembly each and every photon which did originate at the focal point. Two factors which prevent achieving 100% efficiency is the limited solid angle subtended by the collimator assembly and the fact that some of the scattered photons originating from the focal point and within the solid angle subtended by the collimator will be blocked by the collimator. It should be apparent that the larger the solid angle of the collimator the better. We presently believe that a solid angle of about 0.6 steradian is a realistic minimum while about 1.25 is preferred. The solid angle subtended by the collimator, referenced at the focal point, is limited by very practical considerations. The required relative motion necessitates that the collimator cannot occupy space required for that motion nor can it occupy space required by the apparatus producing that motion. Furthermore, the conical collimator is formed of radiation absorbing material and of necessity occupies part of the solid angle subtended by the collimator. To the extent that the radiation absorbing material occupies this region, any scattered photons, even those originating at the focal point, can be absorbed (although unintentionally) by the conical collimator. Using typical dimensions about 30% of the frontal area of the detector will be blocked by the collimator walls. For a collimator subtending about 1.25 steradians relative to the focal spot we estimate an efficiency of about 20%. This is significantly greater than the approximately 1% efficiency of prior art conical collimators. In accordance with one embodiment of the invention, the conical collimator is formed with wall sections having a thickness of about 0.01 to about 0.02 inches. Because of the geometry, even 0.01 inches of suitable materials is sufficient to absorb scattered photons originating from illuminating radiation up to about 300 Kev. Those skilled in the art will realize that higher X-ray energies (such as 1 Mev) may be employed with some increase in wall thickness, where necessary. Typical materials for the conical collimator are tungsten, tantalum, depleted uranium or lead, or compounds thereof and mixtures thereof.

In an embodiment of the invention described herein, the detector assembly moves with the collimator. However, as will be explained, motion of the detector assembly is not essential and the detector assembly may be stationary. Exemplary dimensions of the collimator are 3–5 inches in length with a focal spot 3–5 inches beyond the front of the collimator along the path of the illumination beam.

Some of the typical parameters recited above can be varied within relatively broad limits. In a preferred embodiment, the conical collimator has walls of constant thickness. There are geometrical advantages that can be gained by using walls of tapered thickness, for example, a properly designed tapered conical collimator will have a somewhat smaller effective slice thickness. On the other hand, the price to be paid for this advantage is increased manufacturing complexity and therefore the presently preferred embodiment uses walls of constant thickness.

Likewise, using wall sections thinner than the about 0.01 to 0.02 inches may provide a more efficient collimator (by reducing the blocked frontal area), a smaller slice thickness or a combination of the two. The price to be paid for this advantage is the necessity for using a larger number of cones, each of which is more difficult to fabricate and assemble. Thus it should be understood that whereas the 0.01 to 0.02 inch wall thickness is presently preferred considering the advantages and disadvantages of reducing the wall thickness, it should be understood that wall thicknesses below 0.01 inches are within the scope of the invention.

Likewise, materials that are mentioned above, e.g. tungsten, tantalum, depleted uranium or lead or compounds thereof and mixtures thereof have advantages in rejecting off-axis scatter, other materials which are not as effective have other advantages. For example steel, which is not as good at rejecting off-axis scatter as are the other materials and as a result produces a somewhat poorer signal to noise ratio, on the other hand is advantageous in connection with manufacturability and cost.

Furthermore, as is alluded to above, while the 30% of the frontal area which is blocked using walls of constant thickness and about 0.01 to 0.02 inches in thickness, the blocked frontal area can be reduced below 30% with either thinner wall sections, tapered wall sections or the like. Thus, it should be understood that the invention contemplates blocked frontal areas below the 30% figure.

The invention provides an apparatus useful in tomographic imaging including:

a source of penetrating radiation, means for forming radiation emitted by the source into a beam of defined cross-section and for directing the beam along a path to a target volume, means for supporting an object to be imaged in the target volume so that said beam intercepts said object, a focused collimator located between said target volume and said source, said collimator comprising a plurality of concentric frusto-conical wall sections, adjacent pairs of said wall sections defining scattered radiation transmitting pathways, said pathways originating in a region of said object through which said beam passes, said collimator including an axial passageway coincident with a rotational axis of all said frusto-conical sections and colinear with said path of said radiation beam, and a scattered radiation detector assembly adjacent to said focused collimator and located between said focused collimator and said source, said scattered radiation detector assembly having a central opening to accommodate said path of said radiation beam.

The foregoing apparatus results, at any instant in time, in the detector assembly developing an electrical signal corresponding to the radiation response of that portion of the object located at or adjacent the focal point of the collimator. The radiation response of a sequence of such points is developed by providing relative motion between the object being imaged on the one hand and the radiation source and collimator on the other hand. Thus by scanning the illuminating beam and collimator along a line in space the radiation response of that portion of the object being imaged lying along a line in space defined by a sequence of such points is developed. Orthogonal scanning is also accomplished by providing relative motion between the object on the one hand and the radiation source and collimator on the other hand, to allow detection of the radiation response of that portion of the object lying along or adjacent to a sequence of such lines.

In accordance with another aspect, the invention provides an apparatus useful in backscattered tomographic imaging including: a focused collimator for location between a target volume and a source of penetrating radiation, said collimator comprising a plurality of concentric frusto-conical wall sections, all of said frusto-conical wall sections having a common axis, adjacent pairs of said wall sections defining scattered radiation transmitting pathways, said pathways originating at a common region in said target volume, said collimator including an axial passageway, coincident with said common axis of all said frusto-conical wall sections, and a scattered radiation detector assembly adjacent to said focused collimator and located with said focused collimator between said detector assembly and said target volume, said scattered radiation detector assembly having a central opening encompassing said common axis.

BRIEF DESCRIPTION OF THE DRAWINGS

The present invention will now be further described in the following portions of the specification when taken in conjunction with the attached drawings in which like reference characters identify identical apparatus and in which.

DETAILED DESCRIPTION OF A PREFERRED EMBODIMENT

Figure 1:
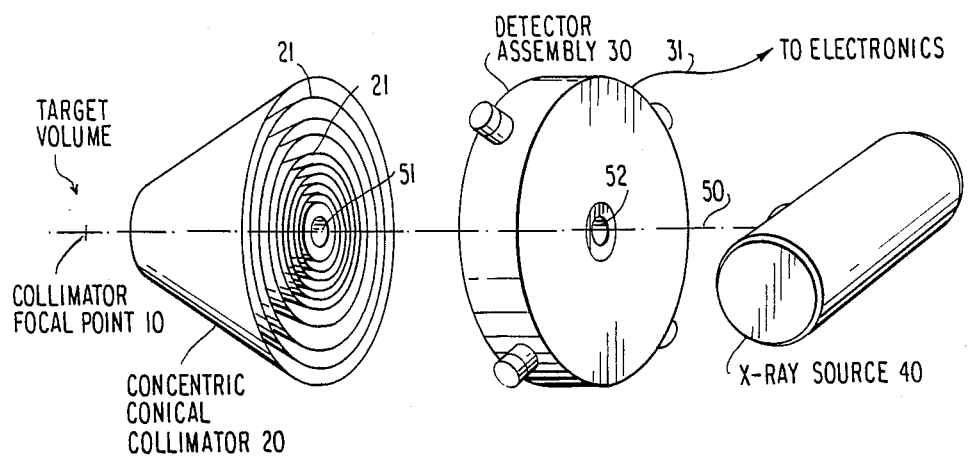
FIG. 1 is a three-dimensional view of the three main components of the invention including the X-ray source, concentric conical collimator and detector assembly.

In order to generate a tomographic image, we must isolate the radiation response of discrete elements or volumes of the object being imaged. By concatenating the radiation response of discrete volumes of the object being imaged, we can accumulate information to generate an image of a slice consisting of the different volume elements. In the copending application, a collimator defines a focal line and a flying spot beam sequentially illuminates different volumes along the focal line. By detecting the radiation energy passing through the collimator, we can determine the radiation response of that one element of the focal line which is illuminated at different instants in time. Thus as the flying spot illuminates the different volumes along the focal line a sequence of signals is developed from the radiation detector corresponding to a "line" portion of the selected slice. By moving the object relative to the focal line, we can accumulate the radiation response of a slice consisting of a sequence of focal lines. A tomographic image in accordance with the present invention is built up in an entirely similar way except that instead of utilizing a focal line, in accordance with the present invention a focal point is employed. Referring to FIG. 1 an X-ray source 40 is illustrated for generating an illumination beam of penetrating radiant energy of defined cross-section and for directing that beam along a path 50 to a target volume; in FIG. 1 the target volume includes the collimator focal point 10, and as is illustrated in FIG. 1, the path 50 of the illuminating radiation passes through the collimator focal point 10. A concentric conical collimator 20 is located between the X-ray source 40 and the target volume. The conical collimator 20 includes an axial passageway 51 which is colinear with the path of the illumination beam 50. The concentric conical collimator 20 comprises a plurality of concentric frusto-conical wall sections 21. Each of the frusto-conical wall sections has a common axis which is coincident with the path 50 of the illuminating radiation. As will be described in more detail below, adjacent pairs of frusto-conical wall sections defines scattered radiation transmitting pathways. Each of the pathways originates in a common region of the object, located in the target volume; specifically, the common region through which the illuminating radiation passes and on which the collimator is focused. The apparatus of FIG. 1 provides for detecting the radiation response of a single volumetric element of the object. Apparatus not specifically illustrated (the electronics) serves to record the response. As will be described below, further apparatus provides for relative motion between the object on one hand and the source/collimator on the other hand. By reason of that motion, different volumetric elements of the object are illuminated and the radiation response is recorded. The sequence of recorded information is then used to develop an image of that slice of the object consisting of the volumetric elements whose response has been recorded.

A detector assembly 30, which can be a conventional scintillator, is arranged between the source 40 and the concentric conical collimator 20 so as to detect X-ray energy which passes through the concentric conical collimator 20.

The collimator 20 is used to focus the view of the detector 30 to a small volumetric element of an object located in the target volume which is irradiated by radiation from the source 40. It should be apparent to those skilled in the art that while an X-ray source is illustrated, other sources of penetrating radiant energy can also be employed.

Figure 2:
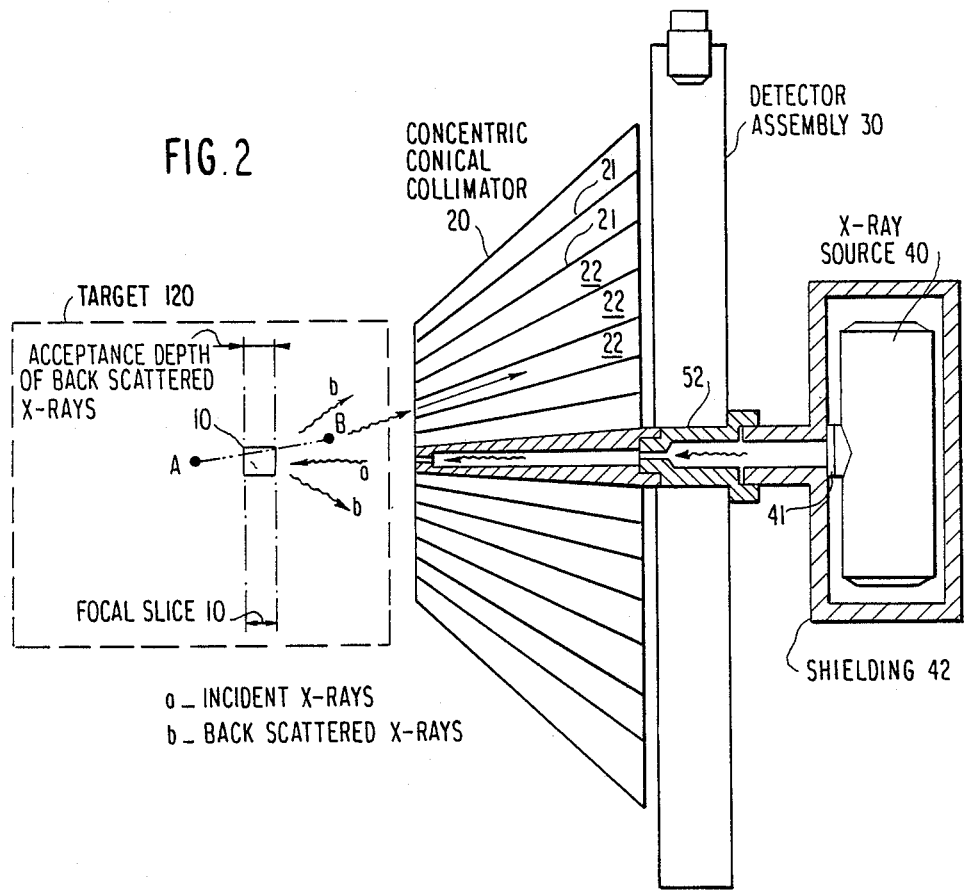
FIG. 2 is a section of FIG. 1 particularly illustrating the internal structure of the collimator in relation to a focal slice.

FIG. 2 is a plan view, in section, of FIG. 1. FIG. 2 shows the X-ray source 40, and the plate 41 which limits the X-ray emission from the source 40 to a beam of predetermined cross-section. The beam travels through a central opening 52 of the detector assembly 30 and then passes through an axial passageway 51 of the collimator 20. In FIG. 2 the incident beam is indicated by the reference characters a. FIG. 2 also shows the focal slice 110 of a target 120 (whose outline is shown dotted). Throughout its passage through the target 120, the X-ray beam 50 produces scatted radiation; this scattered radiation is identified by the reference characters b. Some of the scattered radiation derives from that volume element adjacent the focal spot 10. The walls 21 of the collimator 20 are oriented to allow passage through the scattered radiation transmitting pathways 22 of radiation scattered from the focal spot 10. This scattered radiation will impinge on the detector assembly 30 and be detected. It is the purpose of the collimator 20 to ensure that, to the extent feasible, radiation scattered from other regions of the target 120, outside the focal spot 10 does not reach the detector assembly 30. It is also important to increase the percentage of the energy scattered from the desired volumetric element which is actually detected.

If adjacent walls 21 of the collimator 20 were infinitesimally spaced from each other, then the collimator 20 could truly focus on a "point". However, because of the finite distance between adjacent walls 21, the collimator 20, rather than focusing on a "point" focuses on a volume element, and one dimension of this volume element is the acceptance depth. Those skilled in the art will recognize, that because scattered energy travels in essentially straight lines, singly scattered energy which originates outside the volume element imaged by the collimator 20 will be blocked by the collimator from reaching the detector assembly 30. It is a particular advantage of the conical collimator (as opposed to the linear collimator of the referenced copending application) that it has a greater ability to reject multiply scattered energy. FIG. 2 does show that it is possible for energy scattered at point A, and then at point B to nevertheless pass the collimator 20.

Figure 3:
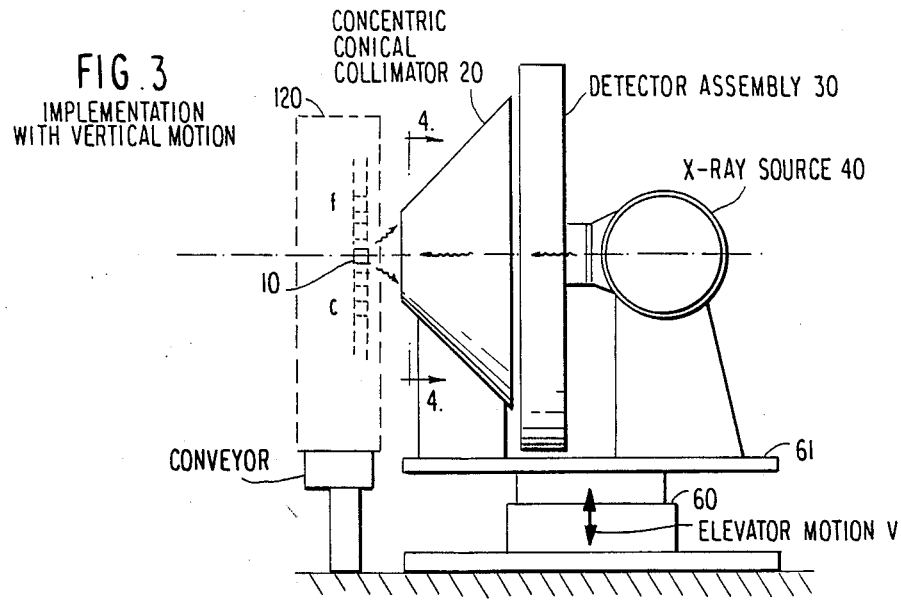
FIG. 3 is a side view of the elements of FIG. 1 showing an elevator for providing relative motion in one direction and a conveyor providing relative motion in a different and substantially perpendicular direction.

FIG. 3, in addition to the components already referred to, also schematically illustrates a conveyor 50 and an elevator 60. The elevator 60 includes a platform 61 which is supported for motion in the direction of the arrow V. The platform supports the source, detector assembly 30 and collimator 20. It is motion of the platform 61 in the direction of the arrow V which provides for the illumination beam 50 scanning a line in space. The conveyor 50 supports the object 120 (shown dotted in FIG. 3) for motion perpendicular to the plane of the illustration. As should be apparent to those skilled in the art, in typical operation the motion of the platform 61 is reciprocating, whereas the motion of the conveyor 50 is linear, and furthermore the velocity of the platform 61 is typically much higher than that of the conveyor 50. The net result of the foregoing is as follows. The illumination beam 50 intercepts the object being imaged 120 and the selected slice 121. At any instant of time a single volume element e of the slice 121 is illuminated. The collimator 20 filters radiation scattered by all illuminated portions of the object 120 to preferentially select only energy scattered in the volume element e, and pass that scattered energy to the detector assembly 30. As the platform 61 moves vertically relative to the object 120, the illumination beam 50 intercepts the object 120 in different lines of sight, one such different line of sight might for example illuminate volume element f in the slice 121. The extent of the motion of the platform 61 defines one dimension of the selected slice, and this may be illuminated over several cycles of movement of the platform 61 with the object 120 substantially stationary relative to the source 40, detector 30 and collimator 20. As the platform 61 reciprocates, the detector assembly outputs a sequence of signals, each corresponding to a different volume element in the slice 121. When the entire dimension of the slice has been scanned (one linear element of the slice), motion of the conveyor 50 allows a different linear element of the slice to be scanned in exactly the same fashion. The detector assembly 30 outputs a different sequence of signals corresponding to a different linear element of the slice. The sequences are recorded by electronics (not illustrated) and a concatenation of each of the sequences is used to generate an image of the selected slice.

While the foregoing embodiment has described linear motion vectors, that is not essential to the invention. Linear motion vectors will generate a slice which can be characterized as planar. However, if the conveyor motion were rotational rather than linear, the slice image would be in the form of a right cylinder. If the reciprocating motion of the platform 60 were inclined relative to the axis of rotation of the element 50, then the slice would be cylindrical but inclined. Other motion vectors would produce still other slice geometries.

Figure 4:
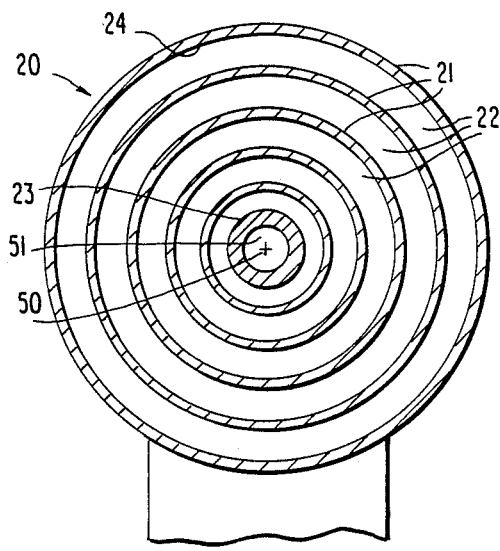
FIG. 4 is a section of a portion of FIG. 3 taken on the line 4—4.

FIG. 4 is a plan cross-section of the collimator at the surface of detector assembly 30. The detector must cover all the passageways 22 so it must extend from the outer extent 23 of the axial passageway 51 to the inner extent 24 of the outermost wall. Of the total area $A_T$ the thickness of the walls 21 blocks D% so the effective area is $(0.01)(D)(A_T)$. A typical value of D is about 30% although we believe even D of 10% is practical.

Figure 5:
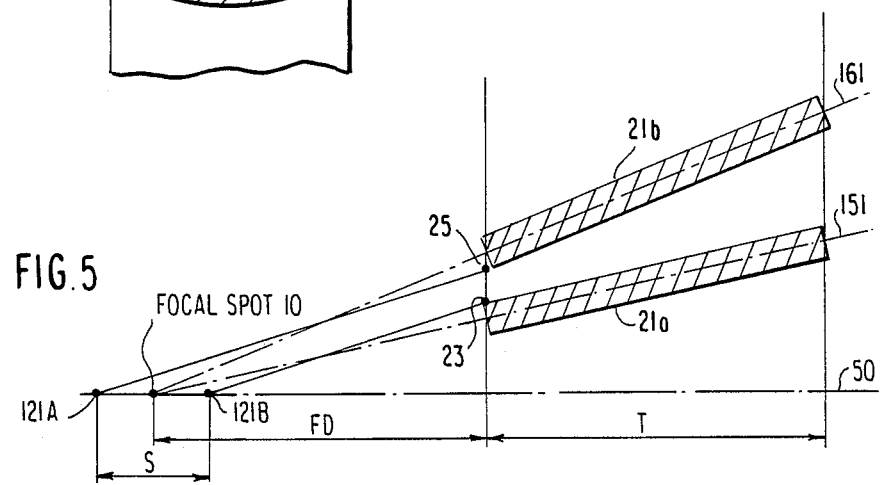
FIG. 5 is a section of FIG. 1 useful in showing the orientation of a pair of adjacent conical walls relative to the focal spot.

FIG. 5 is an elevation section of the collimator 20 illustrating the spacing and separation of two typical wall segments 21a and 21b. The wall thicknesses of the walls 21a and 21b are shown greatly exaggerated, for clarity. FIG. 5 shows, relative to the wall sections 21a and 21b, the illumination beam 50, and the focal spot 10. For a given slice thickness S, collimator thickness T and focal distance FD (between the face of the collimator and the focal spot 10) selection of the spacing of adjacent wall sections 21a and 21b proceeds as follows. The wall section 21a is arranged so that a center line through its cross-section (the line 151) intercepts the focal spot 10. The points 121A and 121B are located along the illumination beam 50 and separated by the slice thickness S. A line is constructed from the point 121B to the upper front corner 23 of the wall 21a. The point 23 can be referred to as the forward outer corner of the wall 21a. It is forward since it is adjacent the face of the collimator 20, the plane through which scattered radiation enters the collimator, and it is outer, since it is an extreme point on the front face of the wall 21a from the illuminating path 50. A line is constructed from the point 121A to the point 25 to be parallel to the line constructed between the points 121B and 23. The point 25 is the forward inner corner of the wall 21b. The wall 21b is oriented relative to its forward inner point 25 so the line through its cross-section, such as the line 161, intercepts the focal spot 10. A simple extension of the foregoing procedure allows the remaining wall sections of the collimator 20 to be located. The foregoing procedure is applicable to both the walls 21 of constant thickness and to similar walls of tapered thickness.

To optimize the imaging, the front face of the collimator 20 is located as close to the object as possible so that the focal length is, in the main, dictated by the depth of the slice within the object. We have also found that the best ratio of FD to T is about unity.

We claim:

1. An apparatus useful in tomographic imaging comprising:
    a source of penetrating radiation, means for forming radiation emitted by said source into a beam of defined cross section and for directing said beam along a path to a target volume,
    means for supporting an object to be imaged in said target volume so that said beam intercepts said object,
    a focused collimator located between said target volume and said source, said collimator comprising a plurality of concentric frusto-conical wall sections, adjacent pairs of said wall sections defining scattered radiation transmitting pathways, said pathways originating in a region of said object through which said beam passes, said collimator including a axial passageway, coincident with a rotational axis of all said frusto-conical sections and colinear with said path of said radiation beam,
    a scattered radiation detector assembly adjacent to said focused collimator and located between said focused collimator and said source, said scattered radiation detector assembly having a central opening to accommodate said path of said radiation beam.

2. An apparatus as recited in claim 1 wherein said concentric wall sections comprise a material selected from Tungsten, Tantalum, depleted Uranium, Lead, compounds thereof and mixtures thereof.

3. An apparatus as recited in claim 1 wherein said radiation detector assembly has an annular cross-section with said opening colinear with said radiation beam and further comprising means for providing relative motion between, on one hand said object and on another hand, said source, said focused collimator and said radiation detector assembly, in a direction perpendicular to said path of said beam.

4. An apparatus as recited in claim 1 wherein said radiation detector assembly has an annular cross-section with said opening colinear with said radiation beam and further comprising means for providing relative motion between, on one hand said object and on another hand said source, said focused collimator and said radiation detector assembly, in two dimensions both perpendicular to said path of said beam.

5. An apparatus as recited in claim 1 wherein said focused collimator subtends a solid angle of at least 0.6 steradians.

6. An apparatus as recited in claim 1 wherein said wall sections have a constant thickness.

7. An apparatus as recited in claim 6 wherein said thickness is about 0.01 inches.

8. An apparatus as recited in claim 6 wherein said thickness is about 0.01 inches to about 0.02 inches.

9. An apparatus as recited in claim 6 wherein said thickness is about 0.01 inches and said focused collimator subtends an angle of at least 0.6 steradians.

10. An apparatus as recited in claim 9 wherein said frustoconical wall sections comprise a material selected from Tungsten, Tantalum, depleted Uranium, Lead, compounds thereof and mixtures thereof.

11. An apparatus useful in backscatter tomographic imaging comprising:
    a source of penetrating radiation means for supporting an object to be imaged so that the object includes a target volume,
    a focused collimator for location between said target volume and said source of penetrating radiation, said collimator comprising a plurality of concentric frusto-conical wall sections, all of said frusto-conical wall sections having a common axis, adjacent pairs of said wall sections defining scattered radiation transmitting pathways, said pathways originating at a common region in said target volume, said collimator including an axial passageway, coincident with said common axis of all said frusto-conical wall sections, and
    a scattered radiation detector assembly adjacent to said focused collimator and located with said focussed collimator between said detector assembly and said target volume, said scattered radiation detector assembly having a central opening to accommodate said common axis.

12. An apparatus as recited in claim 11 wherein said focussed collimator subtends a solid angle of at least about 0.6 steradians referenced at said common region.

13. An apparatus as recited in claim 11 wherein said frustoconical wall sections comprise a material selected from Tungsten, Tantalum, depleted Uranium, Lead, compounds thereof and mixtures thereof.

14. An apparatus as recited in claim 13 wherein said frustoconical wall sections have a thickness of about 0.01 to about 0.02 inches.

15. An apparatus as recited in claim 11 or claim 12 or claim 13 or claim 14 wherein spacing between said walls and wall thickness is selected so that in any cross section perpendicular to said common axis said passageways occupy at least about 10% of an area defined between outermost limits of said collimator and an outer limit of said axial passageway.

* * * * *